United States Patent
Endou et al.

(10) Patent No.: US 7,510,847 B2
(45) Date of Patent: Mar. 31, 2009

(54) KIDNEY-SPECIFIC URATE TRANSPORTER AND GENE THEREOF

(75) Inventors: Hitoshi Endou, Kanagawa (JP); Yoshikatsu Kanai, Tokyo (JP); Atsushi Enomoto, Aichi (JP)

(73) Assignee: Human Cell Systems, Inc., Tokyo (JP)

( * ) Notice: Subject to any disclaimer, the term of this patent is extended or adjusted under 35 U.S.C. 154(b) by 0 days.

(21) Appl. No.: 11/644,193

(22) Filed: Dec. 21, 2006

(65) Prior Publication Data

US 2007/0117162 A1 May 24, 2007

Related U.S. Application Data

(62) Division of application No. 10/485,236, filed as application No. PCT/JP02/08457 on Aug. 22, 2002, now abandoned.

(30) Foreign Application Priority Data

Sep. 21, 2001 (JP) ............................ 2001-29021

(51) Int. Cl.
*G01N 33/566* (2006.01)
*C07K 14/705* (2006.01)
(52) U.S. Cl. ................. 435/7.21; 435/7.2; 436/501
(58) Field of Classification Search ............... None
See application file for complete search history.

(56) References Cited

U.S. PATENT DOCUMENTS

2004/0034192 A1 2/2004 Kato et al.

2006/0035315 A1 2/2006 Yue et al.

FOREIGN PATENT DOCUMENTS

WO WO-01/49728 A2 7/2001
WO WO-01/62923 A2 8/2001

OTHER PUBLICATIONS

Enomoto et al (2002) Nature, 417, 447-452.*
Lagrelius (1981). Acta Obst. Gynoco Scanda. 60, 481-488.*
Gisler et al(2003). Kidney int. 64, 1733-1745.*
Roch-Rame et al (1997). J. Pharm. Exp Therap. 250, 839-845.a.*
Roch-Ramel et al., Journ. of Pharm. and Exper. Therapeutics., vol. 280, No. 2, pp. 839-845 (1997).
Roch-Ramel et al., American Journ. of Physiology, vol. 266, No. 5, Part 2, pp. F797-F805 (1994).
Mori et al., Febs Letters, vol. 417, No. 3, pp. 371-374 (1997).
Enomoto et al., Nature, vol. 417, No. 6887, pp. 447-452 (2002).
Enomoto et al., Accession No. AB071863 (Jun. 5, 2002).
Strausberg, Accession No. AI792236 (Dec. 13, 1999).
Enomoto et al., Nature, vol. 417, pp. 447-452 (2002).
Lipkowitz et al., The Journal of Clinical Investigation, 107(9):1103-1115 (2001).
Race et al., Biochemical and Biophysical Research Communications, 255(2):508-514 (1999).
NIH-MGC, 602107541F1 NC1 CGAP Kid 14 Mus musculus c DNA clone Image:4235795 5', mRNA sequence, GeneBank (Jan. 21, 2001).

* cited by examiner

*Primary Examiner*—John D Ulm
(74) *Attorney, Agent, or Firm*—Edwards Angell Palmer & Dodge LLP; Peter F. Corless; Christine C. O'Day

(57) ABSTRACT

It is intended to identify and provide a novel urate transporter gene participating in the urate transport in the kidney and a urate transporter which is a polypeptide encoded by the above gene. Namely, a protein comprising the amino acid sequence represented by SEQ ID NO:1 or an amino acid sequence derived therefrom by deletion, substitution or addition of one to several amino acids and being capable of transporting uric acid and its analogs; and a gene encoding this protein.

6 Claims, 11 Drawing Sheets

FIG. 11

EXON-INTRON ORGANIZATION OF URAT1 GENE

| EXON | | | INTRON | | | EXON | |
|---|---|---|---|---|---|---|---|
| No. | SIZE(bp) | 3' BINDING SITE | 5' BINDING SITE | SIZE(bp) | No. | 3' BINDING SITE | 5' BINDING SITE | No. |
| 1 | 586 | ...GTGGCCAAG | GTAGGGCCT... | 819 | 1 | ...TCCCATCAG | TGGAACCTC... | 2 |
| 2 | 104 | ...CTCAGACAG | GTGAGTACC. | 521 | 2 | ...GTGCCGCAG | GTTTGGGCG... | 3 |
| 3 | 155 | ...GCACTCTCC | GTAGGTCTC... | 74 | 3 | ...TCCTTGCAG | TGATGGAGT... | 4 |
| 4 | 169 | ...GTACTCCTG | GTGGGTGCT... | 4247 | 4 | ...CCACTTAAG | GTGGCTGGC... | 5 |
| 5 | 124 | ...ACCCCTGAG | GTAAGGCTG... | 167 | 5 | ...CCTCCACAG | GTCTTGCTT... | 6 |
| 6 | 116 | ...GTTGTGCTG | GTAGATGCC... | 751 | 6 | ...CTGCCCCAG | GTTCGCCTT... | 7 |
| 7 | 215 | ...TGCCCCACG | GTGAGGGGG... | 475 | 7 | ...TACCCACAG | AAATGGGGG... | 8 |
| 8 | 109 | ...TGTGCTCAG | GTGAGGCTG... | 258 | 8 | ...CATTGGCAG | GATGACGGC... | 9 |
| 9 | 204 | ...GCAGAACCA | GTGAGTGGA... | 548 | 9 | ...CCTGAACAG | GGCAGTAAA... | 10 |
| 10 | 857 | ...ACAAATGAA | | | | | | |

KIDNEY-SPECIFIC URATE TRANSPORTER AND GENE THEREOF

The present application is a Divisional application of U.S. Ser. No. 10/485,236, filed Jan. 29, 2004, which in turn claimed the prior benefit of International Application No. PCT/JP02/08457, filed Aug. 22, 2002.

TECHNICAL FIELD

The present invention relates to a gene participating in transport of uric acid and analogs thereof or exchange transport of uric acid and the other anion, and a polypeptide encoded by the gene.

BACKGROUND ART

In human race and primates, uric acid which is an organic acid is a final metabolite in purine metabolism in cells, and is excreted mainly from the kidney. In species other than the human race and the primates, it is metabolized to allantoin by an action of uricase in liver, and is excreted from the kidney. Therefore, for the other mammals, it seems that effects of dynamic abnormality of uric acid which is an intermediate product in the kidney on living body are small. Losing the action of uricase in the evolution process seems to be a cause of the fact that the human race has suffered from gout due to hyperuricemia since ancient times.

In humans, when is caused the decrease of uric acid excretion in the kidney causes hyperuricemia, the gout develops at high percentage, which becomes a risk factor for cardiovascular diseases and hypertension. On the other hand, it has been known that the increase of uric acid excretion in the kidney causes renal hypouricemia. Although abnormality of uric acid kinetics is not obvious in these diseases, it has been supposed that urate transporters in the kidney are deeply involved.

The uric acid kinetics in the kidney has been studied by experimental systems using a removed organ perfusion method and an isolated cell membrane vesicle system. In humans, it has been demonstrated that uric acid freely passes through renal glomerulus and thereafter mechanisms for reabsorption and secretion exist in proximal convoluted tubule. However, by the conventional technique, it has been difficult that urate transport system via cell membrane is analyzed in detail, and it has been desired that the transporter per se is isolated and analyzed.

It has been known that there is a remarkable difference among species in the urate transport in the kidney, and there exist the species where secretion is dominant such as swine and rabbit and the species where the reabsorption is dominant such as human, rat and dog. The swine of the species with secretion dominance excretes from 200 to 300% of uric acid per unit nephron, whereas a human of the species with uric acid reabsorption dominance excretes only about 10% of uric acid per unit nephron. Also, it has been known that responses to uricosuric accelerators and uricosuric inhibitors are different even among the species with reabsorption dominance. Accordingly, since the kinetics of uric acid and the responses to drugs in the kidney are different depending on the species, and uric acid is reciprocally transported, it has not been easy to isolate a molecular entity of the urate transporter though its existence has been assumed.

Among the urate transporters in the kidney, the transporters which reabsorb uric acid from renal tubular lumen have been studied for long time by the experimental system using the isolated cell membrane vesicle system. For the drugs currently used for the patients with hyperuricemia and gout, it is assumed that the transporter which reabsorbs uric acid in the kidney is inhibited. Also, it is forecasted that renal hypouricemia is caused due to gene aberration of this transporter.

Recently, it has been demonstrated that the transporters involved in the reabsorption of uric acid are exchange transporters of uric acid and various anions in several experiments. For pyrazinamide used as the first-line drug of antituberculous drugs at present, it has been shown that pyrazine carboxylate which is the metabolite of pyrazinamide is an exchange substrate of this exchange transporter and facilitates the reabsorption of uric acid. That is thought to be the cause of hyperuricemia frequently observed in the patients administered the antituberculous drug.

Accordingly, the transporter involved in the reabsorption of uric acid in the kidney is thought to play an important role for internal kinetics of uric acid. It has been anticipated that elucidation of its molecular entity leads to elucidate a mechanism of action of uricosuric accelerators and a cause of renal hypouricemia, and development of new gout curative medicines.

We have previously isolated and reported organic anion transporters, OAT1 (organic anion transporter) (Sekine, T. et al., J. Biol. Chem., 272:18526-18529, 1997), OAT2 (Sekine, T. et al., FEBS Letter, 429:179-182, 1998), OAT3 (Kusuhara, H. et al., J. Biol. Chem., 274:13675-13680, 1999), and OAT4 (Cha, S. H. et al., J. Biol. Chem., 275:4507-4512, 2000) which play central roles in medicament transport in the kidney, liver, brain, placenta and so on. These transporters belonging to OAT family are the transporters capable of transporting many organic anions with different chemical structures, and also perform the transport of various anionic medicaments.

It was not obvious whether the urate transporter belongs to the known transporter family, but since uric acid is a dibasic acid having both pyrimidine structure and imidazole structure and is one of the organic anions, the possibility that the urate transporter phylogenetically belonges to OAT family was anticipated. In OAT family, since OAT4 exists at the side of renal tubular lumen in the kidney and the existence of the transporter involved in the reabsorption of uric acid is also assumed at the side of renal tubular lumen, it has been also anticipated that the transporter is phylogenetically similar to OAT4.

From these facts, we have anticipated that the urate transporter in the kidney belongs to the organic ion transporter family.

DISCLOSURE OF THE INVENTION

An object of the present invention is to identify and provide a novel urate transporter gene participating in the urate transport in the kidney and a urate transporter which is a polypeptide encoded by the above gene. Other objects will be apparent from the following description.

BRIEF DESCRIPTION OF THE DRAWINGS

FIG. 11 shows exon-intron structure of URAT1 gene in human genome.

BEST MODE FOR CARRYING OUT THE INVENTION

Figure 1:
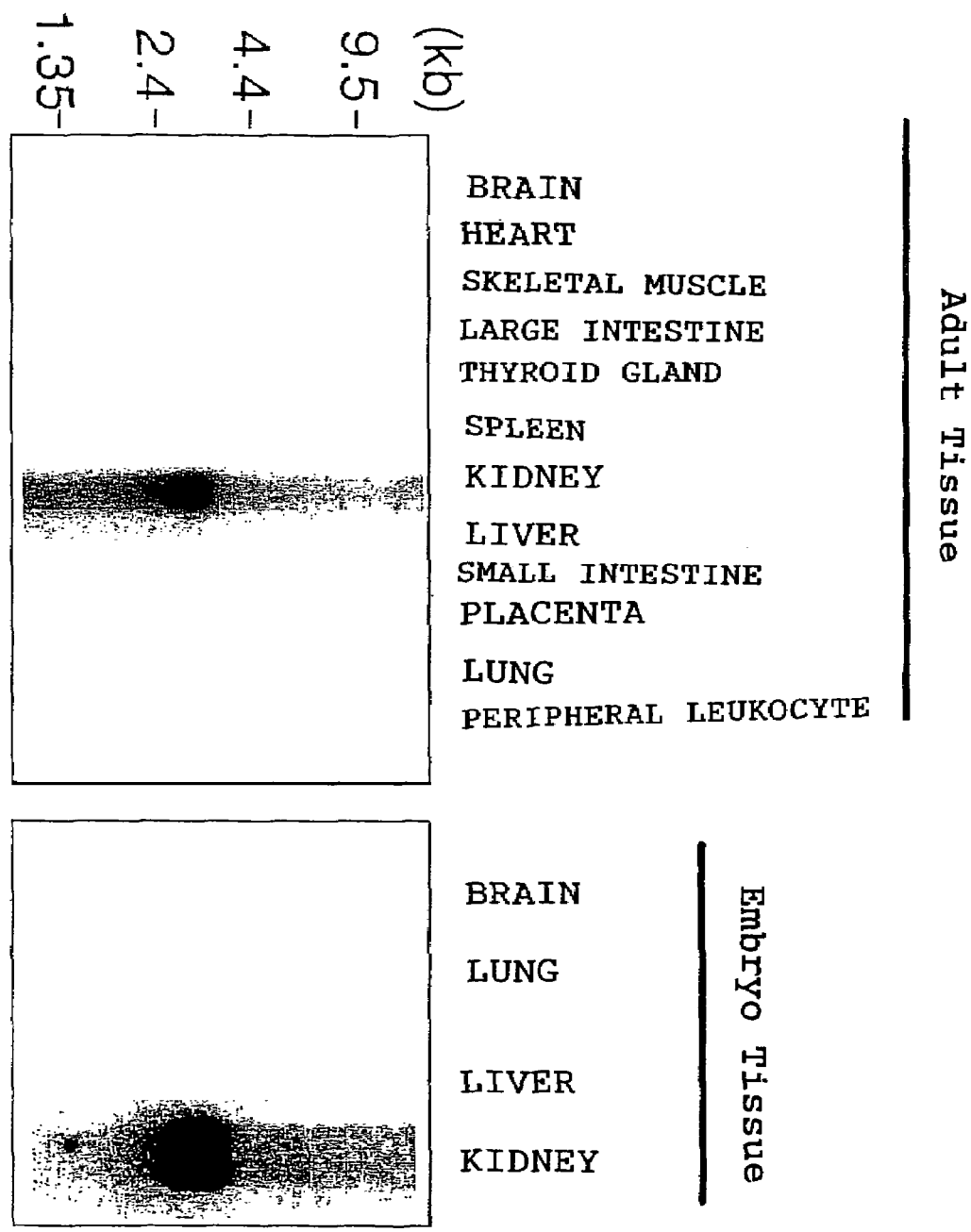
FIG. 1 shows the results of analyzing the expression of URAT1 gene messenger RNA in various organ tissues of human adult and embryo by Northern blotting.

As described above, the present inventors isolated four organic anion transporters, OTA1, OTA2, OTA3 and OTA4. They have about 40% homology of amino acid sequences each other. On the basis of these sequences, disclosed information of human genome project was searched, and multiple novel gene fragments having homology to OAT1, 2, 3 and 4 were identified. Among them, one novel gene fragment extremely closed to a gene locus position of OAT4 was analyzed, and a site supposed to be an initiation codon was identified. A primer specific for 5' upstream of this initiation codon was made, and isolation of this novel gene was attempted by 3'-RACE (3-rapid amplification of cDNA ends) method using messenger RNA derived from various tissues of humans. As a result, a novel clone (URAT1) which had been never reported was identified by the 3'-RACE method using human kidney messenger RNA.

The urate transporter1, URAT1 of the present invention has an ability to transport uric acid and its analogs via cell membrane from one side to the other side and further is a urate/anion exchanger by making the anion at the other side of the cell membrane an exchange substrate.

The protein of the present invention includes, for example, those having the amino acid sequence in which one or several amino acids are deleted, substituted or added in the amino acid sequence represented by SEQ ID NO: 1, in addition to one having the amino acid sequence represented by SEQ ID NO: 1. The amino acids could be deleted, substituted or added to the extent where urate transport activity is not lost, and typically from 1 to about 110 and preferably from 1 to about 55. Such proteins typically have up to 75% and preferably up to 90% homologous amino acid sequences to the amino acid sequence represented by SEQ ID NO: 1.

In the present invention, the isolation of the gene by the 3'-RACE method can be carried out typically by making a primer of about 30 bases specific for guanine- or cytosine-rich gene at the 5' upstream of the initiation codon, performing reverse transcription of tissue-derived messenger RNA using an oligo dT primer with an adapter sequence, and subsequently performing PCR (polymerase chain reaction) using the adapter sequence and the gene-specific primer. It is possible to further enhance accuracy of the PCR by the use of heat resistant polymerase with higher fidelity.

The urate transporter gene of the present invention can be isolated and yielded by screening cDNA library prepared using renal tissues or cells in an appropriate mammal as a gene source. The mammals include human in addition to non-human animals such as dog, cattle, horse, goat, sheep, monkey, swine, rabbit, rat and mouse.

The screening and isolation of the gene can be suitably carried out by homology screening and PCR method.

For the resultant cDNA, it is possible to determine the base sequence by the conventional method, analyze the translation region and determine the amino acid sequence of the protein encoded by this, i.e., URAT1.

It can be verified, for example, by the following method that the obtained gene is cDNA of the urate transporter gene, i.e., a gene product encoded by the cDNA is the urate transporter. The ability to transport (uptake) uric acid into cells can be confirmed by introducing cRNA (complementary RNA) prepared from the obtained URAT1 cDNA into oocyte to express, and measuring the uptake of a substrate into the cells by the conventional uptake experiment using uric acid as the substrate (Sekine, T. et al., Biochem. Biophis. Res. Commun., 251:586-591, 1998).

Also, transport property and substrate specificity of URAT1 can be examined by applying the similar uptake experiment to expressing cells.

Further, the property of URAT1, for example, the property that URAT1 performs the transport with time dependency, substrate selectivity and pH dependency of URAT1 can be examined by applying the similar uptake experiment to the expressing cells.

Homologous genes and chromosomal genes derived from the different tissues or different organisms can be isolated by screening appropriate cDNA libraries or genomic DNA libraries made from the different gene sources using cDNA of the obtained URAT1 gene.

Also, the gene can be isolated from the cDNA library by the conventional PCR method using synthetic primers designed on the basis of the information of the disclosed base sequence of the gene of the present invention (the base sequence represented by SEQ ID NO: 1 or a part thereof).

The DNA libraries such as cDNA library and genomic DNA library can be prepared by the methods described in, for example, "Sambrook, J., Fritsh E. F., and Maniatis, T., "Molecular Cloning" (published by Cold Spring Harbor Laboratory Press in 1989)". Or when there is a commercially available library, it may be used.

To obtain the structure of URAT1 gene on human genome, the genomic DNA library is screened using the obtained URAT1 gene cDNA, and the obtained clones are analyzed. Or the structure may be searched on the basis of the disclosed information of the human genome analysis results using a homology search program.

The urate transporter (URAT1) of the present invention can be produced by gene recombination technology using cDNA which encodes the urate transporter. For example, it is possible to incorporate DNA (cDNA, etc.) which encodes the urate transporter in an appropriate expression vector and introduce the resultant recombinant DNA into appropriate host cells. Expression systems (host vector system) for producing the polypeptide include the expression systems of bacteria, yeast, insect cells and mammalian cells. Among these, to obtain the functional protein, it is desirable to use the insect cells and the mammalian cells.

For example, when the polypeptide is expressed in the mammalian cells, an expression vector is constructed by inserting DNA which encodes the urate transporter in the downstream of an appropriate promoter (e.g., SV40 promoter, LTR promoter, elongation 1α promoter and the like) in an appropriate expression vector (e.g., retroviral vector, papilloma virus vector, vaccinia virus vector, SV40 type vector and the like). Next, the target polypeptide is produced by transforming appropriate animal cells with the obtained expression vector and culturing transformants in an appropriate medium. The mammalian cells as the hosts include cell lines such as monkey COS-7 cells, Chinese hamster CHO cells, human HeLa cells and primary culture cells derived from renal tissues, LLC-PK1 cells derived from swine kidney, OK cells derived from opossum kidney, and proximal convoluted tubule S1, S2 and S3 cells derived from mouse.

As the cDNA which encodes the urate transporter URAT1, it is possible to use the cDNA having the base sequence shown in the sequence 1, and further it is possible to design DNA corresponding to the amino acid sequence and use the DNA which encodes the polypeptide without being limited to the above cDNA. In this case, 1 to 6 codons which encodes one amino acid are known, and the codon used may be optionally selected, but it is possible to design the sequence with high expression by considering use frequency of codons in the host utilized for the expression. The DNA with the designed sequence can be acquired by chemical synthesis of DNA, fragmentation and bind of the above cDNA, partial modification of the base sequence and the like. The artificial partial modification and mutagenesis can be carried out by site specific mutagenesis methods (Mark, D. F. et al., Proc. Natl. Acad. Sci. USA, 18:5662-5666, 1984) utilizing primers including synthetic oligonucleotides which encode the desired modification.

The nucleotides (oligonucleotides or polynucleotides) which hybridize with the urate transporter gene of the present invention under a stringent condition can be used as probes to detect the urate transporter gene, and further can be used, for example, as antisense oligonucleotides, ribozymes and decoys to modulate the expression of the urate transporter. As such nucleotides, it is possible to use, for example, the nucleotides typically comprising the partial sequence of consecutive 14 or more bases or the complementary sequence thereof in the base sequence represented by SEQ ID NO: 1. In order to make the hybridization more specific, as the partial sequence, the longer sequence, e.g., the sequence of 20 or more bases or 30 or more bases may be used.

Also, using the urate transporter of the present invention or the polypeptide having immunological equivalence thereto, it is possible to acquire antibodies thereof, and the antibodies can be utilized for the detection and the purification of the urate transporter. The antibody can be produced by using the urate transporter of the invention, a fragment thereof, or a synthetic peptide having the partial sequence thereof and the like as an antigen. The polyclonal antibody can be produced by the conventional method in which the antigen is inoculated to the host animal (e.g., rat or rabbit) and immunized serum is collected, and the monoclonal antibody can be produced by the conventional technology such as a hybridoma method.

Figure 6:
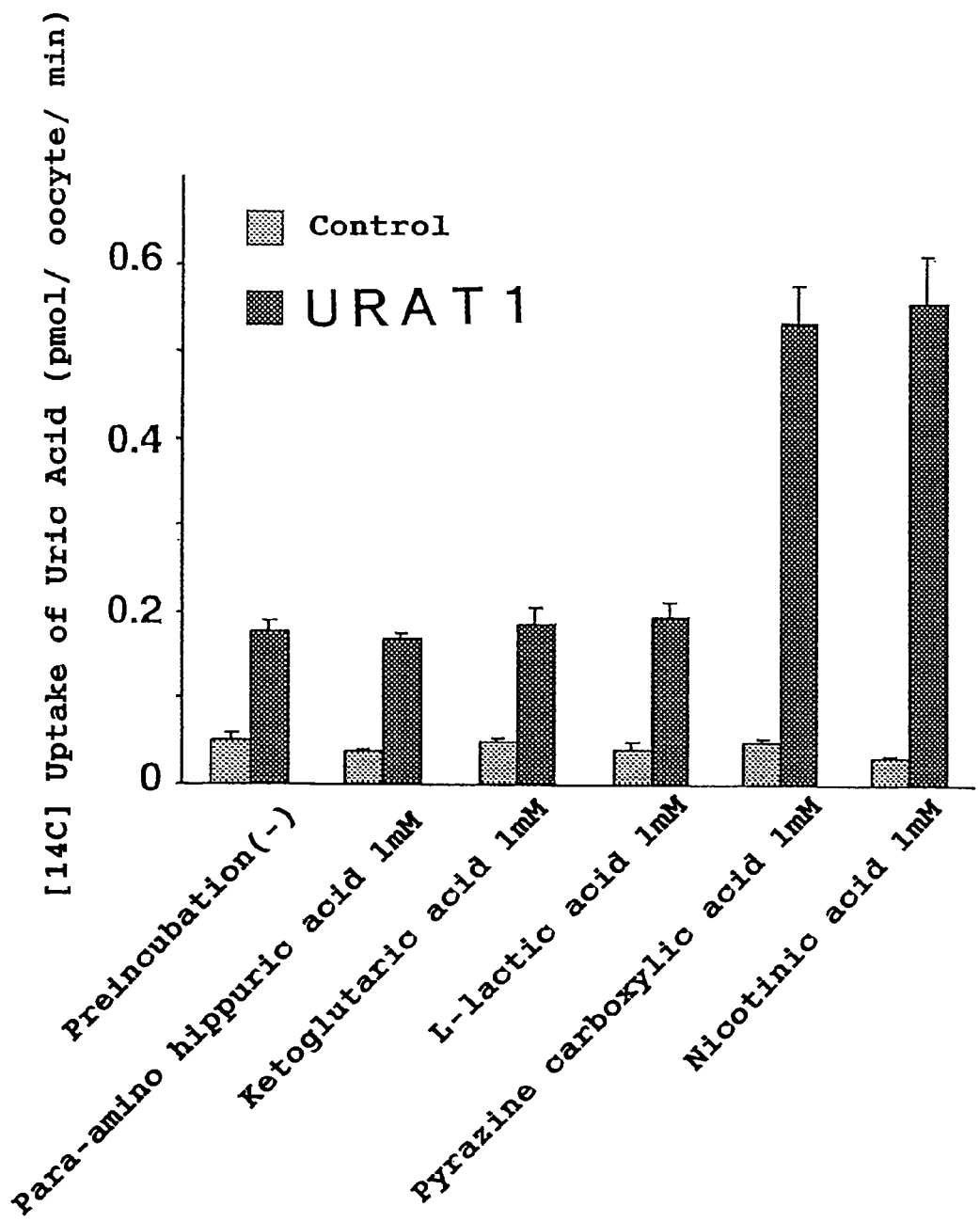
FIG. 6 shows the result of preincubation with various organic acids in uric acid uptake experiments by oocytes injected with cRNA of URAT1 gene.
Figure 8:
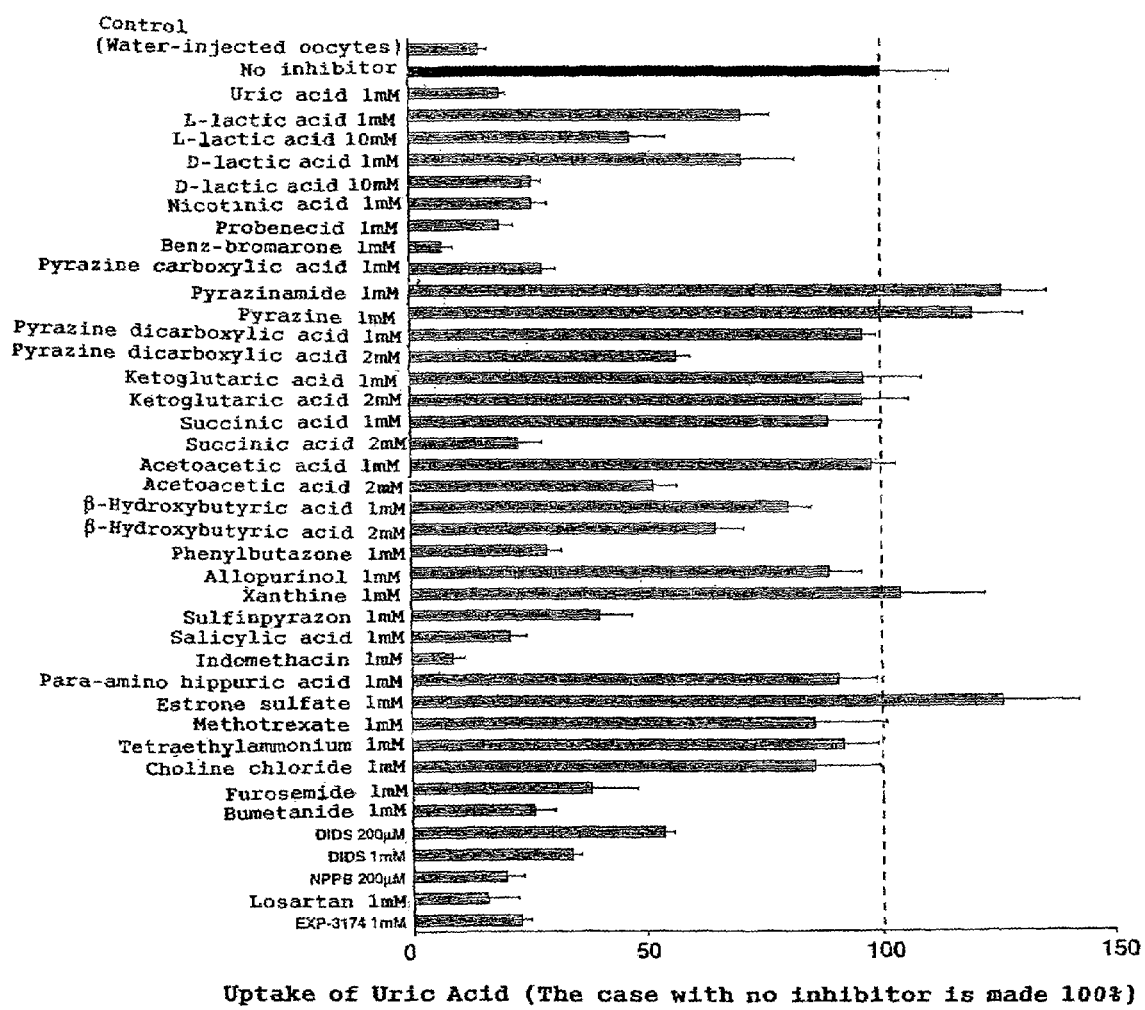
FIG. 8 shows the result of examining the effects of addition of various organic acids or analog compounds thereof to the system in uric acid uptake experiments by oocytes injected with cRNA of URAT1 gene.

Furthermore, the present invention provides a screening method of a substance having uricosuric accelerating action. The protein of the invention works for transporting uric acid into the cells and is deeply involved in the reabsorption of uric acid. Also, as is shown in FIGS. 6, 8, 9 and 10, it is possible to quantify the accelerating or inhibiting action for uric acid uptake of the screening substance in the system where the protein of the invention is expressed, by adding uric acid to the system, further adding the screening substance thereto, and comparing a uric acid uptake amount with that in the case with no addition of the screening substance. As is shown in FIGS. 6 and 8, the substances clinically used as uricosuric accelerators have remarkably inhibited the uptake of uric acid in the above experimental system, and thus, it is shown that it become possible to screen the uricosuric accelerating action of the screening substance in this system. As the cells used in this screening system, the cells are not limited to oocytes used in the following experiments, and it is possible to use various living cells as long as the cells can express the protein of the invention.

Therefore, the present invention provides the method for screening substances having uricosuric regulating action using the protein of the invention. As the uricosuric regulating actions, there are the uricosuric accelerating action and the uricosuric inhibiting action, and those having the uricosuric accelerating action are preferable for the treatment/prevention of hyperuricemia and gout. Thus, the preferable uricosuric regulating action includes the uricosuric accelerating action. Moreover, the present invention provides uricosuric regulators screened by the above screening method. The preferable uric acid regulator includes a uricosuric accelerators. The uricosuric regulator screened by the method of the invention can regulate the uptake of uric acid by the urate transporter involved in the urate transport in the kidney, and therefore can be used as an active ingredient of the medicines for the treatment/prevention of various diseases associated with the reabsorption of uric acid such as hyperuricemia and gout.

It is possible to make the obtained active ingredient a pharmaceutical composition using a pharmacologically acceptable carrier.

EXAMPLES

The present invention is described in more detail by examples below, but these examples do not limit the invention.

In the following examples, unless otherwise specified, respective manipulations were carried out by the methods described in "Sambrook, J., Fritsch E. F., and Maniatis, T., "Molecular Cloning" (published by Cold Spring Harbor Laboratory Press in 1989)" or when using commercially available kits, they were used according to the instructions of the commercially available articles.

Example 1

Isolation of Kidney-Specific Urate Transporter (URAT1) cDNA and Analysis Thereof On the basis of the base sequence information of OAT1, OAT2, OAT3 and OAT4 already isolated by the present inventors, the disclosed analysis results of the human genome project were searched using the homology search program. As a result, multiple novel gene fragments having homology to OAT1, OAT2, OAT3 and OAT4 were obtained. Among them, one of the novel gene fragments extremely close to the locus position of OAT4 was analyzed, and the site thought to be the initiation codon was identified in it. This initiation codon was identified by comparing the novel gene fragments with gene sequences of OAT1 and OAT4.

A primer specific for the 5' upstream region of the predicted initiation codon was made using 28 bases, and the isolation of this novel gene was attempted by 3'-RACE (3'-rapid amplification of cDNA ends) method using messenger RNA derived from various tissues of human. As a result, a monoclone (URAT1) was obtained by the 3'-RACE method using human kidney messenger RNA. A single band obtained by PCR method was subcloned in pCRII-TOPO vector using TA cloning method, and further subcloned in pcDNA 3.1(+) vector which was the expression vector. As a result, a novel cDNA (URAT1 cDNA) which has urate transport activity was obtained (for analysis of transport function, see the followings.).

Determination of the base sequence of the c DNA (URAT1 cDNA) obtained by the above was carried out using specific primers by an automatic sequencer (manufactured by Applied Biosystems) (described in SEQ ID NO:1).

The expression of URAT1 gene was analyzed in various tissues of human (Northern blotting) (FIG. 1). Full length URAT1 cDNA was labeled with $^{32}$P-dCTP, and using this as a probe, hybridization was carried out using filters (manufactured by Clontech) blotting RNA extracted from various human tissues. The hybridization was carried out overnight in a hybridization solution comprising the labeled full length URAT1 cDNA, and the filters were washed with 0.1×SSC comprising; 0.1% SDS at 65° C. As a result of Northern blotting, an intensive band was detected in the renal tissue. In human embryonic tissues, the band was detected in the kidney.

Example 2

Analysis of Urate Transporter Functions

From plasmid comprising URAT1 cDNA, cRNA (RNA complementary to cDNA) was prepared in vitro using T7 RNA polymerase (see Sekine, T., et al., J. Biol. Chem., 272: 18526-18529, 1997).

Figure 2:
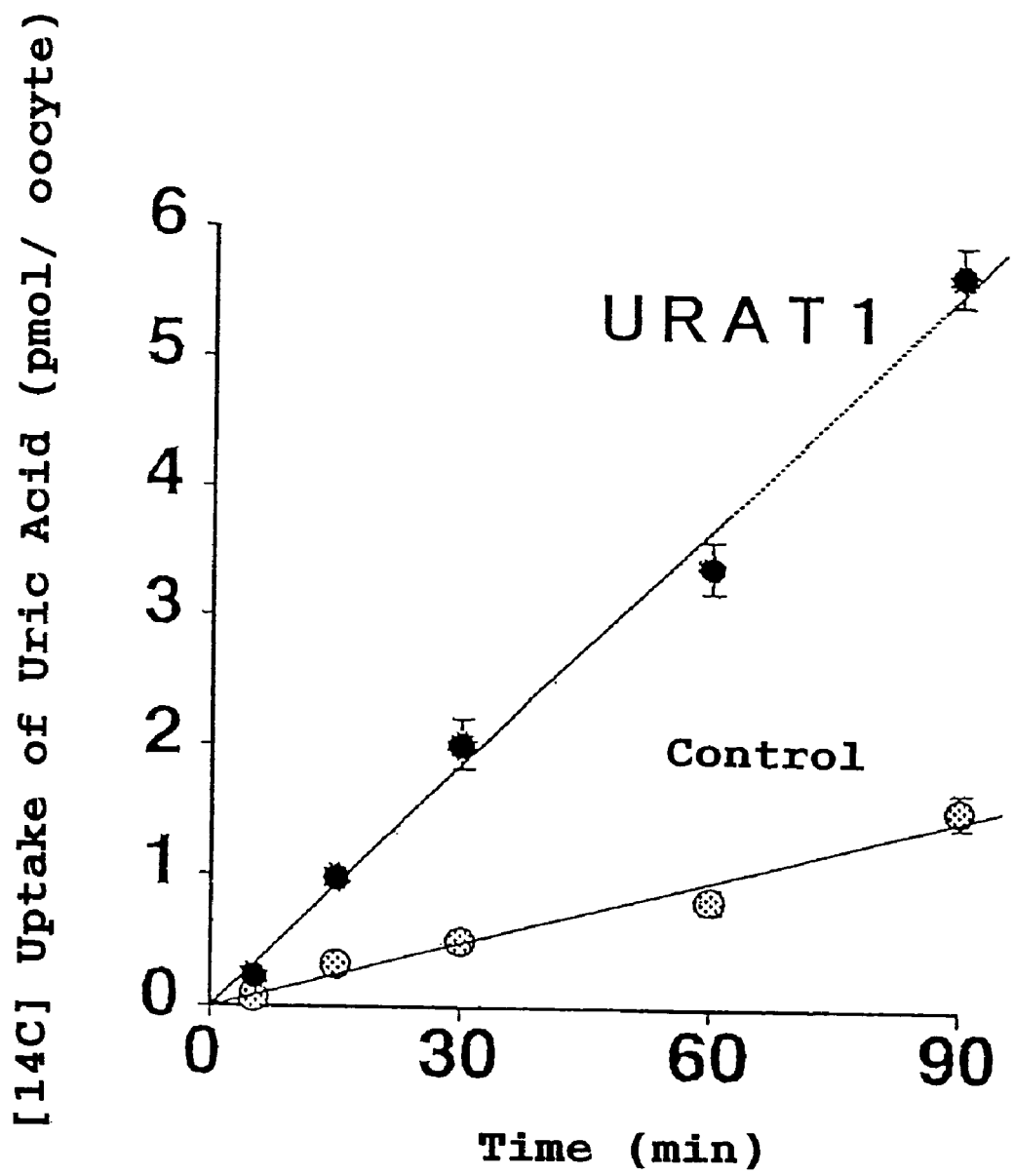
FIG. 2 shows the result of time dependency in uric acid uptake experiments by oocytes injected with cRNA of URAT1 gene.

The resultant cRNA was injected in oocytes of platanna, and uptake experiments of the radiolabeled uric acid in these oocytes were carried out according to the method already reported (Sekine, T., et al., J. Biol. Chem., 272:18526-18529, 1997). As a result, it was found that the oocytes in which URAT1 was expressed showed uptake of [$^{14}$C] uric acid as shown in FIG. 2. The oocytes in which URAT1 was expressed showed time dependency in the uptake of [$^{14}$C] uric acid. This indicated that not only URAT1 was bound to uric acid but also was the transporter to transport it into the cells. No uptake of [$^{14}$C] PAH (para-amino hippuric acid) and [$^{14}$C] TEA (tetraethylammonium) which are a representative substrate of the organic ion transporter family was observed (not shown).

Figure 3:
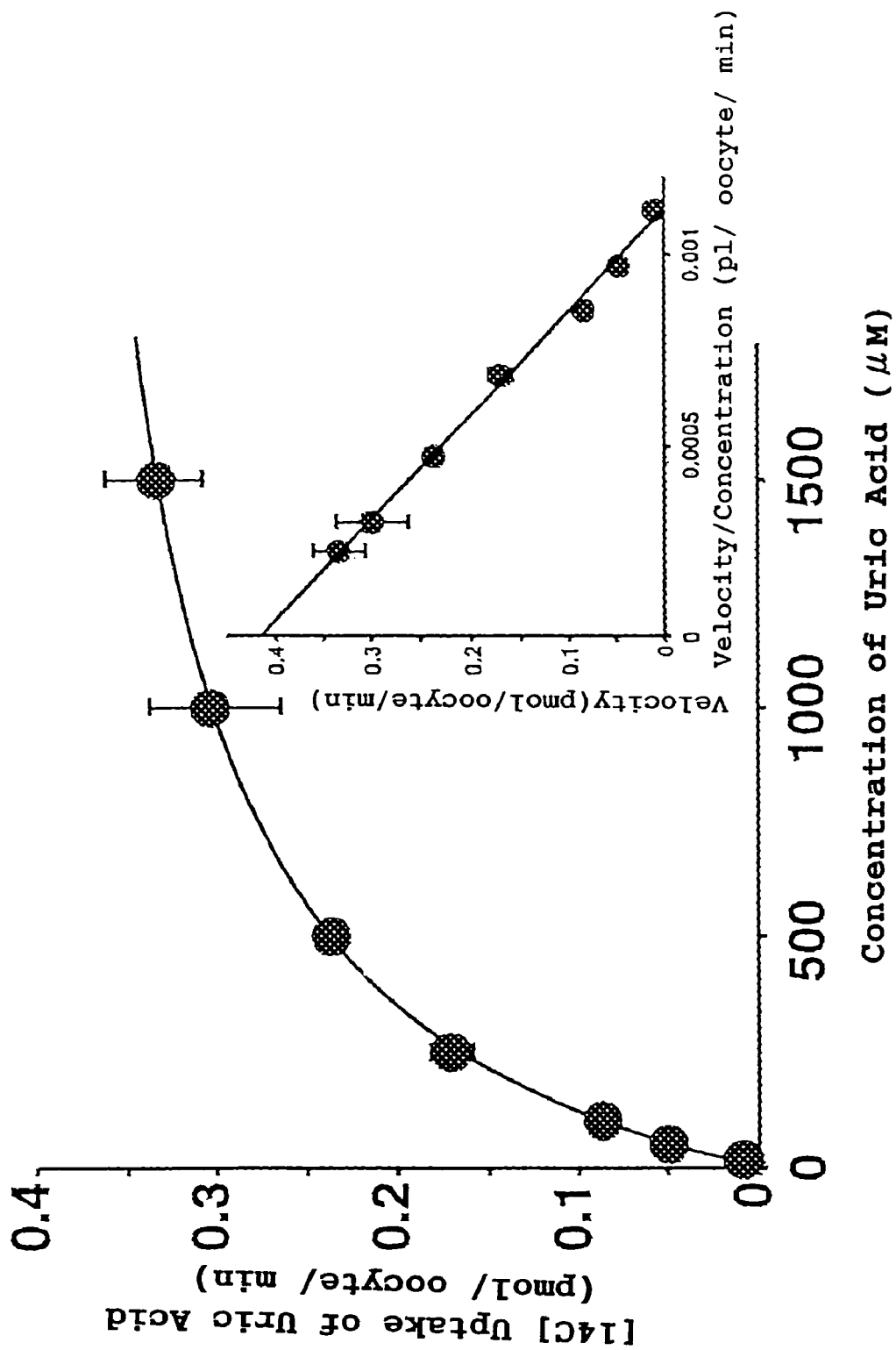
FIG. 3 shows the result of concentration dependency in uric acid uptake experiments by oocytes injected with cRNA of URAT1 gene.

Michaelis-Menten dynamic experiment in urate transport by URAT1 was carried out. Concentration dependency of uric acid in the transport by URAT1 was studied by examining change of uptake amounts of uric acid at various concentrations by URAT1. The uptake experiment of the radiolabeled uric acid was carried out using oocytes injected with URAT1 cRNA according to the method described above. As a result (FIG. 3), Km value (Michaelis constant number) of the uric acid uptake was approximately 372±25 μM.

Figure 4:
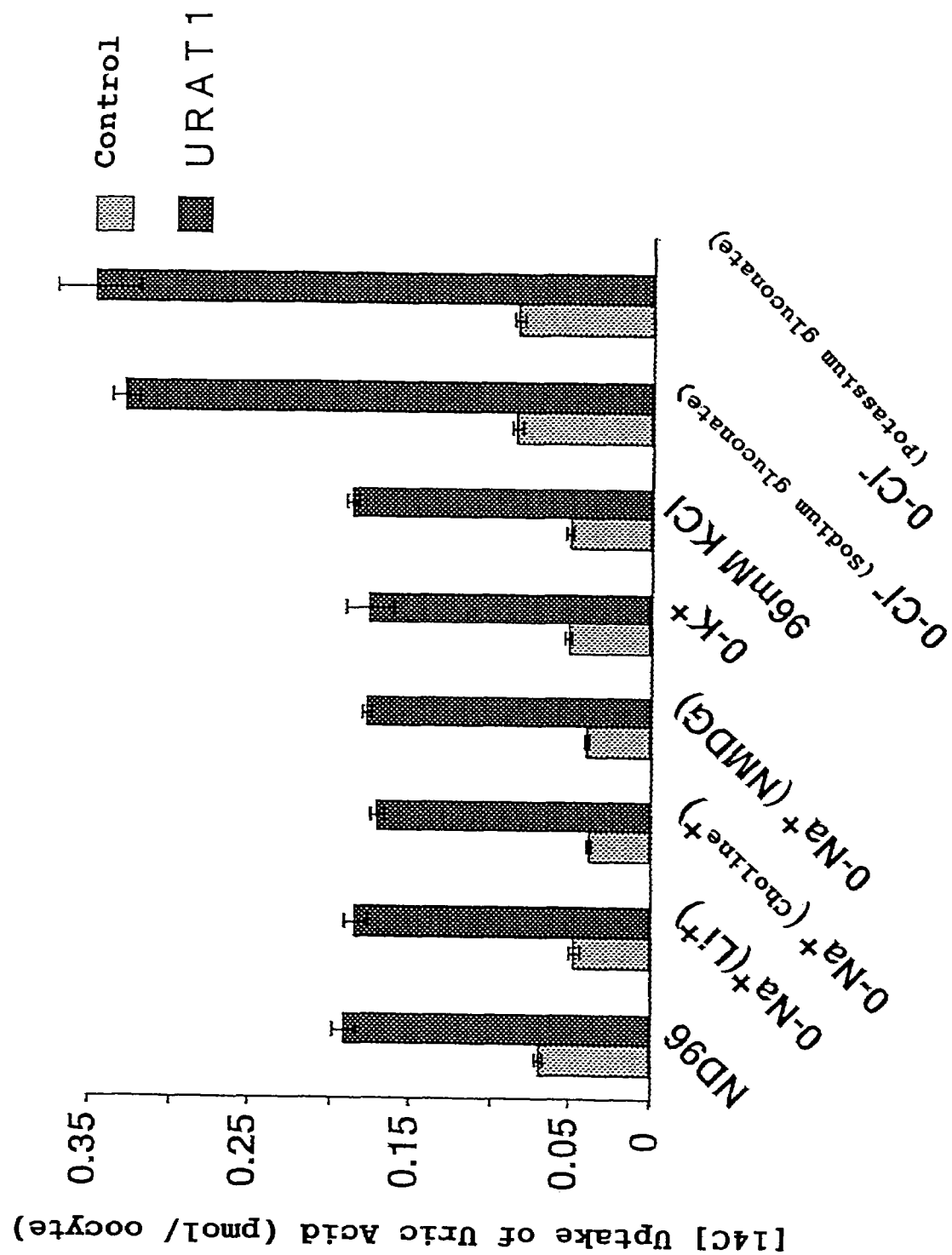
FIG. 4 shows the result of examining the effects of added salts in uric acid uptake experiments by oocytes injected with cRNA of URAT1 gene.

The effect of various electrolytes on the urate transport by URAT1 was studied. (FIG. 4). When extracellular sodium was replaced with lithium, choline and N-methyl-D-glucamine (NMDG), the urate transport via URAT1 was not changed. It was demonstrated that URAT1 was the extracellular sodium-independent urate transporter. When extracellular potassium ions were completely replaced with sodium (0–K+ in FIG. 4) and sodium was completely replaced with the potassium ions (96 mM KCl), the urate transport was not also changed, which was demonstrated that URAT1 was cell membrane potential-independent. When extracellular chloride ions were replaced with gluconic acid, the uptake of uric acid was significantly increased. From the experimental system using the isolated cell membrane vesicle system, the presence of the exchanger for uric acid and chloride was shown at the side of renal tubular lumen in human kidney. Thus, this experimental result suggests that chloride might be the exchange substrate of uric acid.

Figure 5:
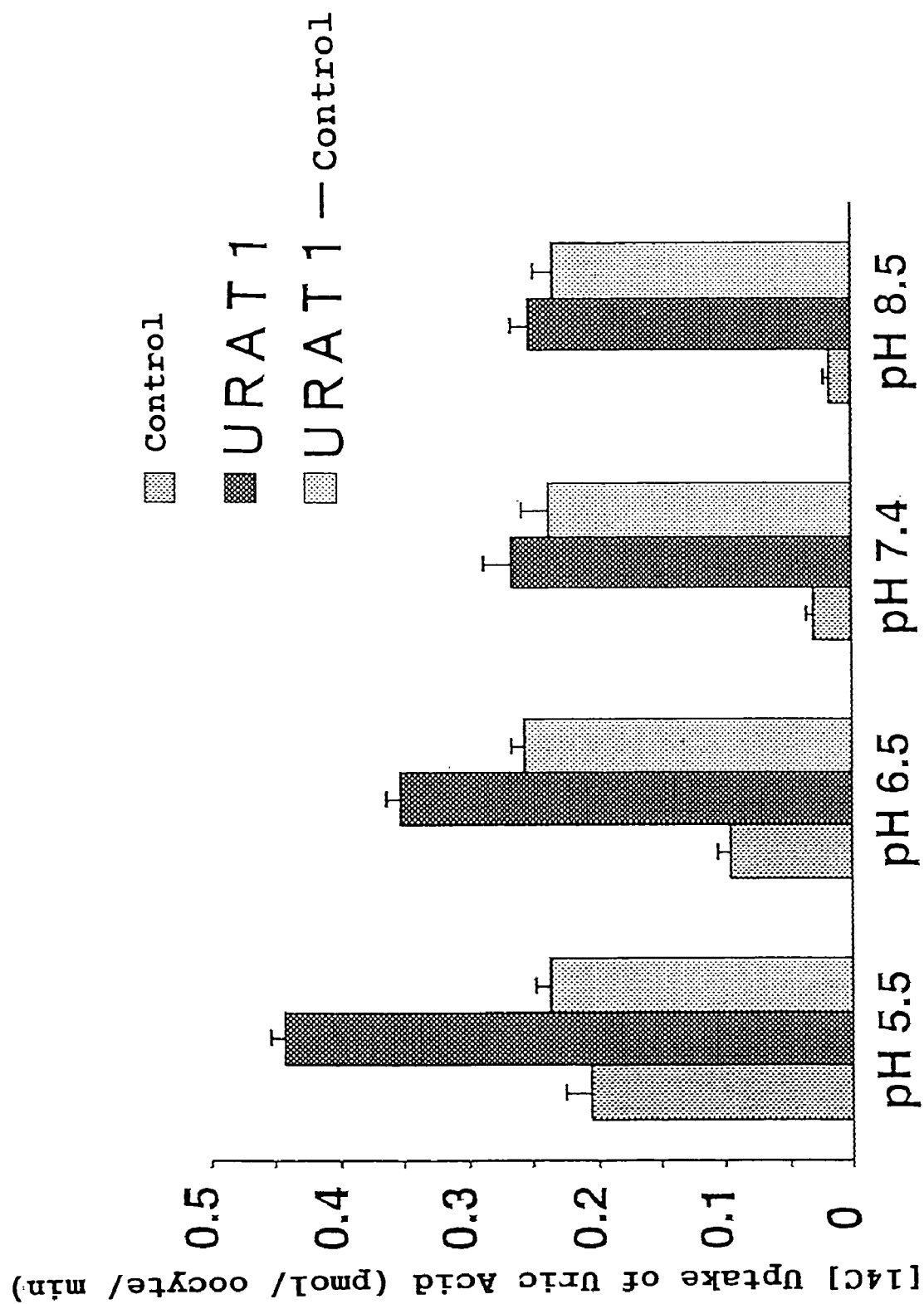
FIG. 5 shows the result of pH dependency in uric acid uptake experiments by oocytes injected with cRNA of URAT1 gene.

The pH dependency in the urate transport by URAT1 was studied. As shown in FIG. 5, when the extracellular pH was acidified, the urate transport in the oocyte injected with URAT1 cRNA was increased, but this seems to be caused by non-specific absorption of uric acid in the oocytes injected with water (control). The substantial urate transport (URAT1-control) was not changed depending on pH.

Example 3

Study on Exchange Substrate of Uric Acid in the Urate Transporter

From the experimental system using the isolated cell membrane vesicle system, it has been suggested that monocarboxylic acids such as lactic acid and nicotinic acid can be the exchange substrate of uric acid in the uric acid/anion exchanger in the human kidney. In order to study the exchange substrate of uric acid in URAT1, the oocytes were preincubated with these monocarboxylic acids (1 mM), para-amino hippuric acid and ketoglutaric acid, and subsequently the transport of uric acid was measured (FIG. 6). When the oocytes were preincubated with lmM of pyrazine carboxylic acid and nicotinic acid (3-pyridine carboxylic acid), the uptake of uric acid was significantly increased in the oocytes injected with URAT1 cRNA. On the other hand, when the oocytes were preincubated with para-amino hippuric acid and ketoglutaric acid which were not monocarboxylic acids, the uptake of uric acid was not facilitated. The above results indicate that monocarboxylic acids such as pyrazine carboxylic acid and nicotinic acid are the exchange substrate of uric acid.

Figure 7:
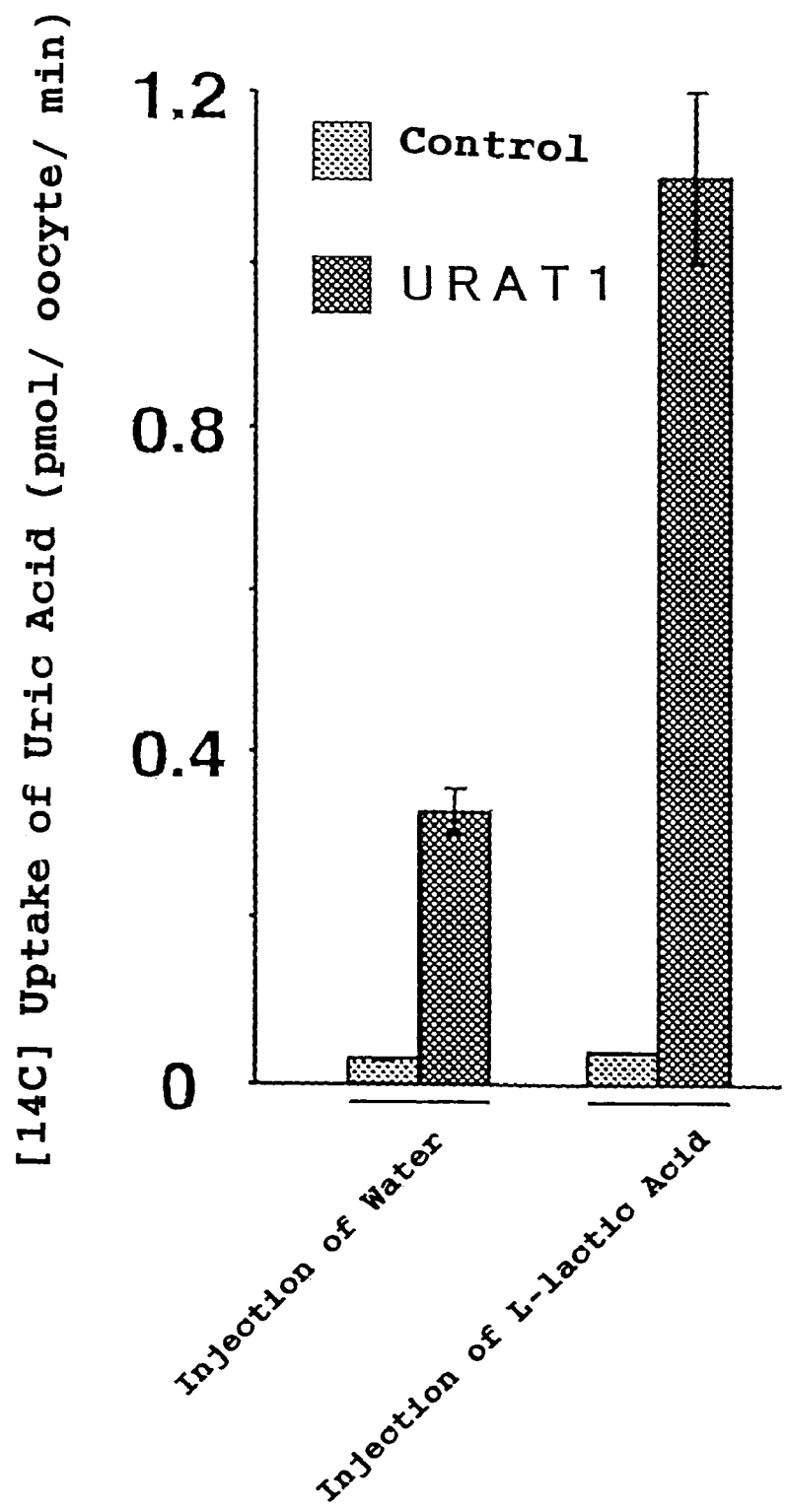
FIG. 7 shows the result of examining the effect of previously injected unlabeled lactic acid (100 mM, 10 nl) in uric acid uptake experiments by oocytes injected with cRNA of URAT1 gene.

In FIG. 6, when the oocytes were preincubated with lactic acid which was monocarboxylic acid, the uptake of uric acid was not facilitated. It was thought to be occurred because the incorporated lactic acid was transported outside of the cells via a pathway other than URAT1 due to abundant expression of endogenous lactate transporters in the oocytes. Also, it was anticipated that low affinity of lactic acid to URAT1 as shown below was also one of the causes. Therefore, 100 nl of 100 mM non-radiolabeled L-lactic acid was precedently injected in the oocytes, and then the uptake of the radiolabeled uric acid was observed (FIG. 7). When lactic acid was precedently injected, the significantly high uptake of uric acid was observed compared to the case where water was injected. Even when para-amino hippuric acid and ketoglutaric acid were injected, no change was observed compared to the case where water was injected (not shown).

From the results in FIGS. 6 and 7, URAT1 is the exchanger of uric acid and monocarboxylic acid. Pyrazinamide which is an antituberculous drug is metabolized to become pyrazine carboxylic acid, which is then excreted into urine, whereas it is said to facilitate the reabsorption of uric acid. The above result shows that as a result of the exchange of uric acid and pyrazine carboxylic acid in URAT1, the uptake of uric acid is facilitated. Accordingly the mechanism to cause hyperuricemia has been demonstrated which is a side effect of pyrazinamide which is the antituberculous drug.

Example 4

Screening of Inhibitory Substance for Urate Transporter

In order to further study substrate selectivity of URAT1, in the uptake experiment system of [$^{14}$C] uric acid by the oocytes injected with URAT1 cRNA, various substances were added to the system and their effects were examined (inhibitory experiments). The uptake experiment of [$^{14}$C] uric acid was carried out using the oocytes injected with URAT1 cRNA according to the method described above (FIGS. 8, 9 and 10). The uptake of 50 µM [$^{14}$C] uric acid was measured under the condition at pH 7.4 in the presence and absence of various compounds (unlabeled) at the concentrations shown in FIG. 8. As a result, various monocarboxylic acids (L-lactic acid, D-lactic acid, nicotinic acid, pyrazine carboxylic acid) significantly inhibited the transport of [$^{14}$C] uric acid by URAT1 (FIG. 8). Ketoglutaric acid which was dicarboxylic acid and could be the exchange substrate of OAT1 did not inhibit under the condition at pH 7.4. Pyrazine dicarboxylic acid which had a similar structure to pyrazine carboxylic acid showed slightly weak inhibitory effect. Anionic and cationic substances such as para-amino hippuric acid and tetraethylammonium did not show any inhibitory action (FIG. 8).

Medicines used for the treatment of hyperuricemia, such as probenecid, benz-bromarone, sulfinpyrazon and phenylbutazone, significantly inhibited the uptake of uric acid in URAT1. Losartan which is a drug for the treatment of hypertension and has been known to have the uricosuric accelerating action, significantly inhibited the uptake of uric acid by URAT1 as well as its metabolite, EXP-3174. From the above results, URAT1 is an action site of representative uricosuric accelerators clinically used at present.

Figure 9:
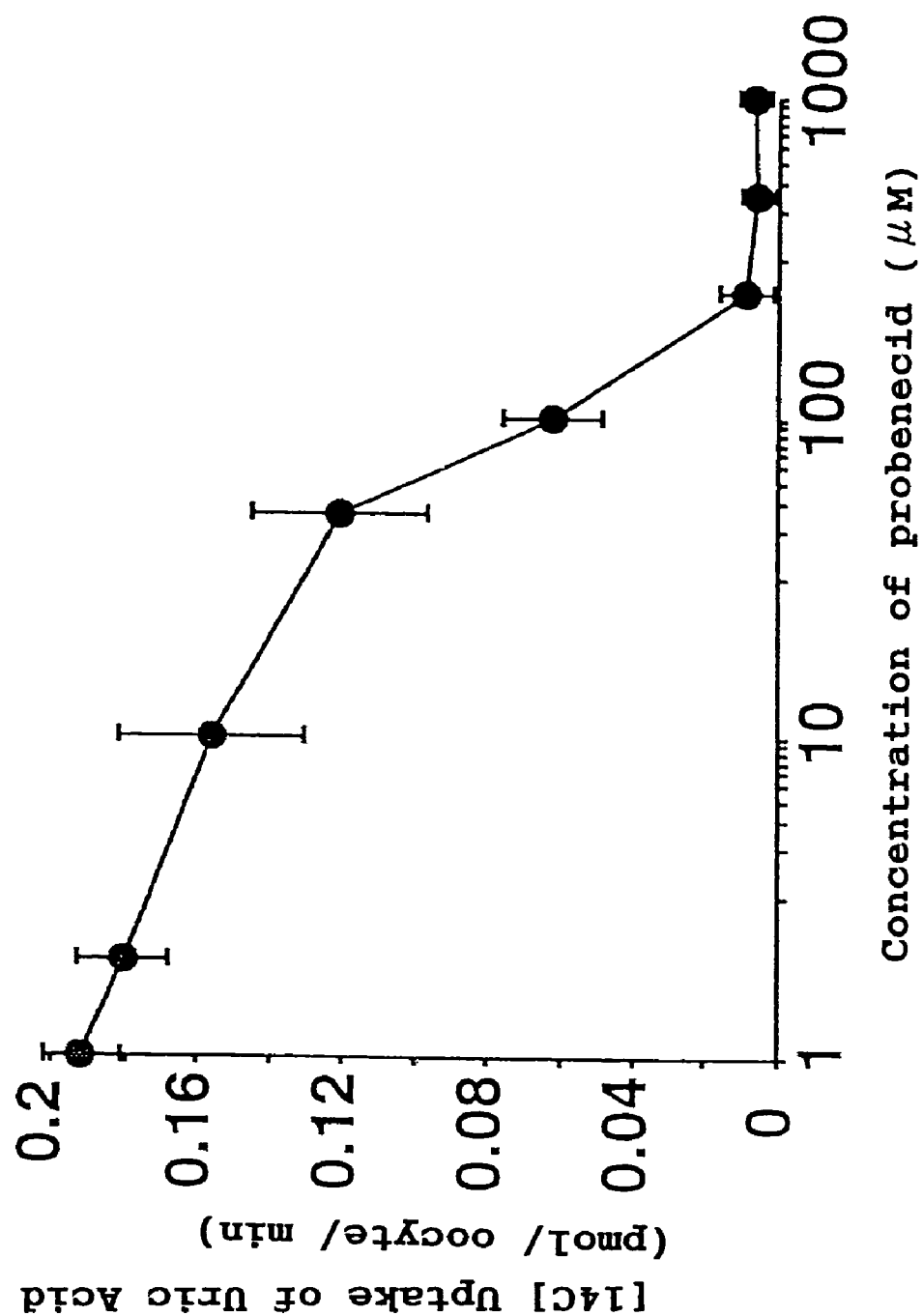
FIG. 9 shows the result of examining the effects of probenecid addition at various concentrations to the system in uric acid uptake experiments by oocytes injected with cRNA of URAT1 gene.
Figure 10:
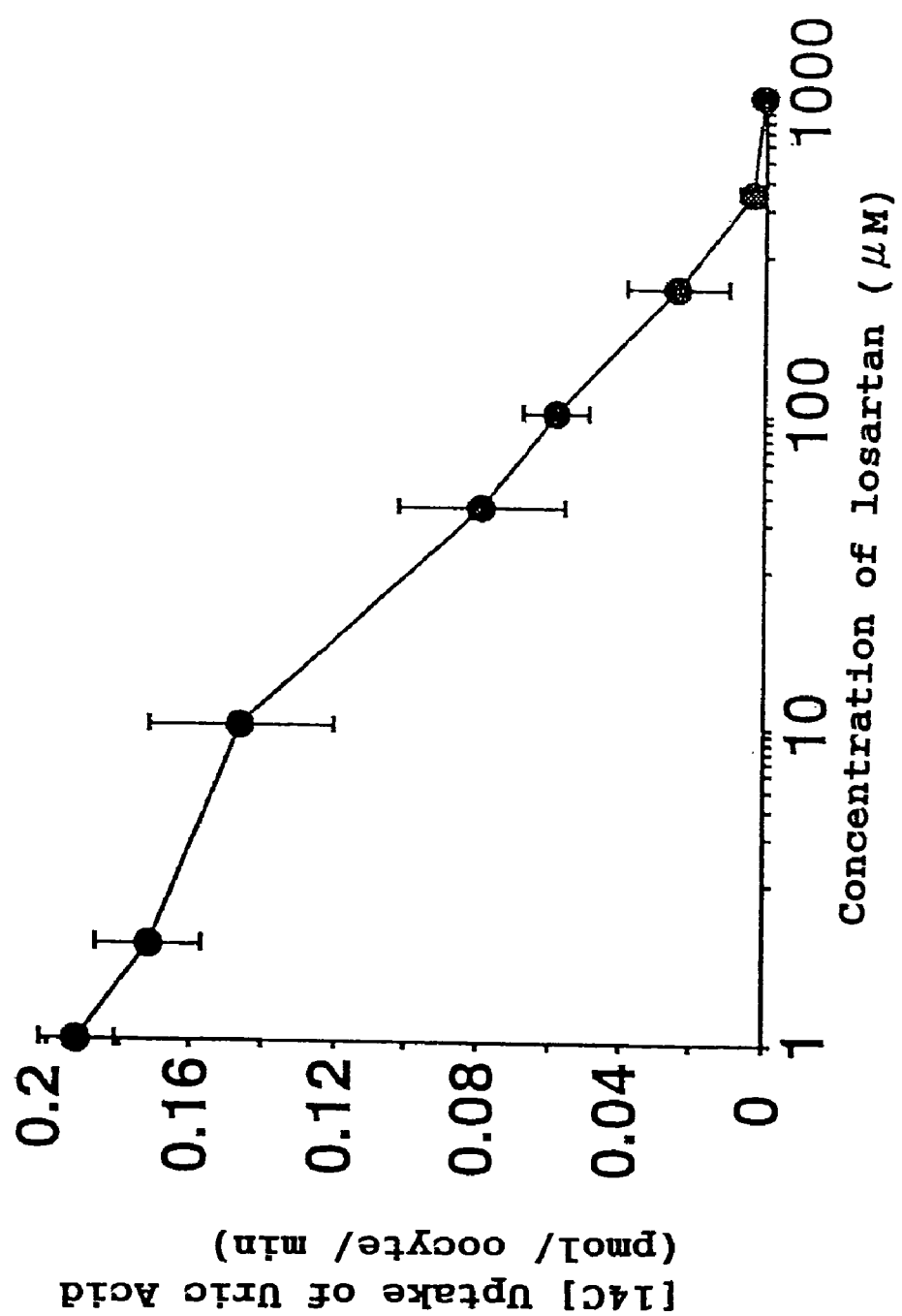
FIG. 10 shows the result of examining the effects of losartan addition at various concentrations to the system in uric acid uptake experiments by oocytes injected with cRNA of URAT1 gene.

The inhibitory effects on the uptake action of uric acid via URAT1 were examined using probenecid and losartan at various concentrations (FIGS. 9 and 10). Their IC50 values were approximately 50 µM and 20 µM, respectively.

Example 5

Structural Analysis of URAT1 Gene

The structure of URAT1 gene in the human genome was analyzed. The disclosed information of the human genome analysis results was searched using the homology search program, and the exon-intron structure of the URAT1 gene was demonstrated. As shown in FIG. 11, the URAT1 gene was consisted of 10 exons and the initiation codon existed in the first exon.

INDUSTRIAL APPLICABILITY

The kidney-specific urate transporter which selectively transports uric acid of the present invention and its gene enable to study in vitro the transport of uric acid and its analogs at the site where the transporter is expressed and forecast internal kinetics of the compounds based on the study. Uric acid is the factor deeply involved in hyperuricemia and gout, and it appears that the invention of the transporter will contribute the elucidation of pathogenesis of hyperuricemia and gout in future. The transporter has the action to reabsorb uric acid in the kidney, and it appears that the transporter will contribute the elucidation of causative gene of renal hypouricemia where reabsorption mechanism of uric acid is lost. Additionally, the elucidation of novel compounds inhibiting the function of the transporter and control factors modulating the expression can contribute the development of new therapeutic methods for hyperuricemia and gout.

The invention claimed is:

1. A method for screening a substances having uricosuric regulating action, which comprises:
   a) providing a transformed cell expressing a recombinant protein consisting of the amino acid sequence of SEQ ID NO: 2;
   b) incubating the substance and uric acid with said cell; and
   c) determining an uptake of uric acid by the cell;
   thereby screening a substance having uricosuric regulating action.

2. The method of claim 1, wherein the amount of uric acid uptake is compared to a cell incubated with no addition of the substance.

3. The method of claim 1, wherein the cell is a mammalian cell.

4. The method of claim 1, wherein the cell is an oocyte.

5. The method of claim 1, wherein the regulating action is a uricosuric accelerating action.

6. The method of claim 1, wherein the regulating action is a uricosuric inhibiting action.

* * * * *

SEQUENCE LISTING

```
<160> NUMBER OF SEQ ID NOS: 2

<210> SEQ ID NO 1
<211> LENGTH: 2642
<212> TYPE: DNA
<213> ORGANISM: Homo sapiens
<220> FEATURE:
<221> NAME/KEY: CDS
<222> LOCATION: (148)..(1806)

<400> SEQUENCE: 1
gccccgagtc tgtgaagcct agccgctggg ctggagaagc cactgtgggc accaccgtgg      60
gggaaacagg cccgttgccc tggcctcttt gccctgggcc agcctttgtg aagtgggccc     120
ctcttctggg ccccttgagt aggttcc atg gca ttt tct gaa ctc ctg gac ctc    174
                                Met Ala Phe Ser Glu Leu Leu Asp Leu
                                  1               5 gtg ggt ggc ctg ggc agg ttc cag gtt ctc cag acg atg gct ctg atg       222
Val Gly Gly Leu Gly Arg Phe Gln Val Leu Gln Thr Met Ala Leu Met
 10              15                  20                  25 gtc tcc atc atg tgg ctg tgt acc cag agc atg ctg gag aac ttc tcg       270
Val Ser Ile Met Trp Leu Cys Thr Gln Ser Met Leu Glu Asn Phe Ser
                 30                  35                  40 gcc gcc gtg ccc agc cac cgc tgc tgg gca ccc ctc ctg gac aac agc       318
Ala Ala Val Pro Ser His Arg Cys Trp Ala Pro Leu Leu Asp Asn Ser
```

```
                 45                  50                  55
acg gct cag gcc agc atc cta ggg agc ttg agt cct gag gcc ctc ctg     366
Thr Ala Gln Ala Ser Ile Leu Gly Ser Leu Ser Pro Glu Ala Leu Leu
            60                  65                  70 gct att tcc atc ccg ccg ggc ccc aac cag agg ccc cat cag tgc cgc     414
Ala Ile Ser Ile Pro Pro Gly Pro Asn Gln Arg Pro His Gln Cys Arg
 75                  80                  85 cgc ttc cgc cag cca cag tgg cag ctc ttg gac ccc aat gcc acg gcc     462
Arg Phe Arg Gln Pro Gln Trp Gln Leu Leu Asp Pro Asn Ala Thr Ala
 90                  95                 100                 105 acc agc tgg agc gag gcc gac acg gag ccg tgt gtg gat ggc tgg gtc     510
Thr Ser Trp Ser Glu Ala Asp Thr Glu Pro Cys Val Asp Gly Trp Val
                110                 115                 120 tat gac cgc agc atc ttc acc tcc aca atc gtg gcc aag tgg aac ctc     558
Tyr Asp Arg Ser Ile Phe Thr Ser Thr Ile Val Ala Lys Trp Asn Leu
            125                 130                 135 gtg tgt gac tct cac gct ctg aag ccc atg gcc cag tcc atc tac ctg     606
Val Cys Asp Ser His Ala Leu Lys Pro Met Ala Gln Ser Ile Tyr Leu
            140                 145                 150 gct ggg att ctg gtg gga gct gct gcg tgc ggc cct gcc tca gac agg     654
Ala Gly Ile Leu Val Gly Ala Ala Ala Cys Gly Pro Ala Ser Asp Arg
            155                 160                 165 ttt ggg cgc agg ctg gtg cta acc tgg agc tac ctt cag atg gct gtg     702
Phe Gly Arg Arg Leu Val Leu Thr Trp Ser Tyr Leu Gln Met Ala Val
170                 175                 180                 185 atg ggt acg gca gct gcc ttc gcc cct gcc ttc ccc gtg tac tgc ctg     750
Met Gly Thr Ala Ala Ala Phe Ala Pro Ala Phe Pro Val Tyr Cys Leu
                190                 195                 200 ttc cgc ttc ctg ttg gcc ttt gcc gtg gca ggc gtc atg atg aac acg     798
Phe Arg Phe Leu Leu Ala Phe Ala Val Ala Gly Val Met Met Asn Thr
                205                 210                 215 ggc act ctc ctg atg gag tgg acg gcg gca cgg gcc cga ccc ttg gtg     846
Gly Thr Leu Leu Met Glu Trp Thr Ala Ala Arg Ala Arg Pro Leu Val
            220                 225                 230 atg acc ttg aac tct ctg ggc ttc agc ttc ggc cat ggc ctg aca gct     894
Met Thr Leu Asn Ser Leu Gly Phe Ser Phe Gly His Gly Leu Thr Ala
            235                 240                 245 gca gtg gcc tac ggt gtg cgg gac tgg aca ctg ctg cag ctg gtg gtc     942
Ala Val Ala Tyr Gly Val Arg Asp Trp Thr Leu Leu Gln Leu Val Val
250                 255                 260                 265 tcg gtc ccc ttc ttc ctc tgc ttt ttg tac tcc tgg tgg ctg gca gag     990
Ser Val Pro Phe Phe Leu Cys Phe Leu Tyr Ser Trp Trp Leu Ala Glu
                270                 275                 280 tcg gca cga tgg ctc ctc acc aca ggc agg ctg gat tgg ggc ctg cag    1038
Ser Ala Arg Trp Leu Leu Thr Thr Gly Arg Leu Asp Trp Gly Leu Gln
            285                 290                 295 gag ctg tgg agg gtg gct gcc atc aac gga aag ggg gca gtg cag gac    1086
Glu Leu Trp Arg Val Ala Ala Ile Asn Gly Lys Gly Ala Val Gln Asp
            300                 305                 310 acc ctg acc cct gag gtc ttg ctt tca gcc atg cgg gag gag ctg agc    1134
Thr Leu Thr Pro Glu Val Leu Leu Ser Ala Met Arg Glu Glu Leu Ser
            315                 320                 325 atg ggc cag cct cct gcc agc ctg ggc acc ctg ctc cgc atg ccc gga    1182
Met Gly Gln Pro Pro Ala Ser Leu Gly Thr Leu Leu Arg Met Pro Gly
330                 335                 340                 345 ctg cgc ttc cgg acc tgt atc tcc acg ttg tgc tgg ttc gcc ttt ggc    1230
Leu Arg Phe Arg Thr Cys Ile Ser Thr Leu Cys Trp Phe Ala Phe Gly
            350                 355                 360 ttc acc ttc ttc ggc ctg gcc ctg gac ctg cag gcc ctg ggc agc aac    1278
```

```
                Phe Thr Phe Phe Gly Leu Ala Leu Asp Leu Gln Ala Leu Gly Ser Asn
                            365                 370                 375 atc ttc ctg ctc caa atg ttc att ggt gtc gtg gac atc cca gcc aag            1326
Ile Phe Leu Leu Gln Met Phe Ile Gly Val Val Asp Ile Pro Ala Lys
        380                 385                 390 atg ggc gcc ctg ctg ctg ctg agc cac ctg ggc cgc cgc ccc acg ctg            1374
Met Gly Ala Leu Leu Leu Leu Ser His Leu Gly Arg Arg Pro Thr Leu
395                 400                 405 gcc gca tcc ctg ttg ctg gcg ggg ctc tgc att ctg gcc aac acg ctg            1422
Ala Ala Ser Leu Leu Leu Ala Gly Leu Cys Ile Leu Ala Asn Thr Leu
410                 415                 420                 425 gtg ccc cac gaa atg ggg gct ctg cgc tca gcc ttg gcc gtg ctg ggg            1470
Val Pro His Glu Met Gly Ala Leu Arg Ser Ala Leu Ala Val Leu Gly
                430                 435                 440 ctg ggc ggg gtg ggg gct gcc ttc acc tgc atc acc atc tac agc agc            1518
Leu Gly Gly Val Gly Ala Ala Phe Thr Cys Ile Thr Ile Tyr Ser Ser
                445                 450                 455 gag ctc ttc ccc act gtg ctc agg atg acg gca gtg ggc ttg ggc cag            1566
Glu Leu Phe Pro Thr Val Leu Arg Met Thr Ala Val Gly Leu Gly Gln
        460                 465                 470 atg gca gcc cgt gga gga gcc atc ctg ggg cct ctg gtc cgg ctg ctg            1614
Met Ala Ala Arg Gly Gly Ala Ile Leu Gly Pro Leu Val Arg Leu Leu
475                 480                 485 ggt gtc cat ggc ccc tgg ctg ccc ttg ctg gtg tat ggg acg gtg cca            1662
Gly Val His Gly Pro Trp Leu Pro Leu Leu Val Tyr Gly Thr Val Pro
490                 495                 500                 505 gtg ctg agt ggc ctg gcc gca ctg ctt ctg ccc gag acc cag agc ttg            1710
Val Leu Ser Gly Leu Ala Ala Leu Leu Leu Pro Glu Thr Gln Ser Leu
                510                 515                 520 ccg ctg ccc gac acc atc caa gat gtg cag aac cag gca gta aag aag            1758
Pro Leu Pro Asp Thr Ile Gln Asp Val Gln Asn Gln Ala Val Lys Lys
                525                 530                 535 gca aca cat ggc acg ctg ggg aac tct gtc cta aaa tcc aca cag ttt            1806
Ala Thr His Gly Thr Leu Gly Asn Ser Val Leu Lys Ser Thr Gln Phe
                540                 545                 550 tagcctcctg aggaacctgc gatgggacgg tcagaggaag agacttcttc tgttctctgg          1866
agaaggcagg aggaaagcaa agacctccat ttccagaggc ccagaggctg ccctctgagg          1926
tccccactct cccccagggc tgcccctcca ggtgagccct gccctctca cagtccaagg           1986 ggccccttc aatactgaag gggaaaagga cagtttgatt ggcaggaggt gacccagtgc           2046
accatcaccc tgcccgccc tcgtggcttc ggagagcaga ggggtcaggc caggggaac            2106 gagctggcct tgccaaccct ctgcttgact ccgcactgcc acttgtcccc ccacacccgt          2166
ccacctgccc agagctcaga gctaaccacc atccatggtc aagacctctc ctagctccac          2226
acaagcagta gagtctcagc tccacagctt tacccagaag ccctgtaagc ctggcccctg          2286
gcccctcccc atgtccctcc aggcctcagc cacctgcccg ccacatcctc tgcctgctgt          2346 cccccttccca ccctcatccc tgaccgactc cacttaaccc ccaaacccag cccccttcc          2406 aggggtccag ggccagcctg agatgcccgt gaaactccta cccacagtta cagccacaag          2466
cctgcctcct cccacccctgc cagcctatga gttcccagag ggttgggca gtcccatgac          2526 cccatgtccc agctccccac acagcgctgg gccagagagg cattggtgcg agggattgaa          2586
taaagaaaca aatgaaaaaa aaaaaaaaaa aaaaaaaaaa aaaaaaaaaa aaaaaa              2642
```

<210> SEQ ID NO 2
<211> LENGTH: 553
<212> TYPE: PRT

<213> ORGANISM: Homo sapiens

<400> SEQUENCE: 2

```
Met Ala Phe Ser Glu Leu Leu Asp Leu Val Gly Gly Leu Gly Arg Phe
  1               5                  10                  15

Gln Val Leu Gln Thr Met Ala Leu Met Val Ser Ile Met Trp Leu Cys
             20                  25                  30

Thr Gln Ser Met Leu Glu Asn Phe Ser Ala Ala Val Pro Ser His Arg
         35                  40                  45

Cys Trp Ala Pro Leu Leu Asp Asn Ser Thr Ala Gln Ala Ser Ile Leu
     50                  55                  60

Gly Ser Leu Ser Pro Glu Ala Leu Leu Ala Ile Ser Ile Pro Pro Gly
 65                  70                  75                  80

Pro Asn Gln Arg Pro His Gln Cys Arg Arg Phe Arg Gln Pro Gln Trp
                 85                  90                  95

Gln Leu Leu Asp Pro Asn Ala Thr Ala Thr Ser Trp Ser Glu Ala Asp
            100                 105                 110

Thr Glu Pro Cys Val Asp Gly Trp Val Tyr Asp Arg Ser Ile Phe Thr
        115                 120                 125

Ser Thr Ile Val Ala Lys Trp Asn Leu Val Cys Asp Ser His Ala Leu
    130                 135                 140

Lys Pro Met Ala Gln Ser Ile Tyr Leu Ala Gly Ile Leu Val Gly Ala
145                 150                 155                 160

Ala Ala Cys Gly Pro Ala Ser Asp Arg Phe Gly Arg Arg Leu Val Leu
                165                 170                 175

Thr Trp Ser Tyr Leu Gln Met Ala Val Met Gly Thr Ala Ala Ala Phe
            180                 185                 190

Ala Pro Ala Phe Pro Val Tyr Cys Leu Phe Arg Phe Leu Leu Ala Phe
        195                 200                 205

Ala Val Ala Gly Val Met Met Asn Thr Gly Thr Leu Leu Met Glu Trp
    210                 215                 220

Thr Ala Ala Arg Ala Arg Pro Leu Val Met Thr Leu Asn Ser Leu Gly
225                 230                 235                 240

Phe Ser Phe Gly His Gly Leu Thr Ala Ala Val Ala Tyr Gly Val Arg
                245                 250                 255

Asp Trp Thr Leu Leu Gln Leu Val Val Ser Val Pro Phe Phe Leu Cys
            260                 265                 270

Phe Leu Tyr Ser Trp Trp Leu Ala Glu Ser Ala Arg Trp Leu Leu Thr
        275                 280                 285

Thr Gly Arg Leu Asp Trp Gly Leu Gln Glu Leu Trp Arg Val Ala Ala
    290                 295                 300

Ile Asn Gly Lys Gly Ala Val Gln Asp Thr Leu Thr Pro Glu Val Leu
305                 310                 315                 320

Leu Ser Ala Met Arg Glu Glu Leu Ser Met Gly Gln Pro Pro Ala Ser
                325                 330                 335

Leu Gly Thr Leu Leu Arg Met Pro Gly Leu Arg Phe Arg Thr Cys Ile
            340                 345                 350

Ser Thr Leu Cys Trp Phe Ala Phe Gly Phe Thr Phe Gly Leu Ala
        355                 360                 365

Leu Asp Leu Gln Ala Leu Gly Ser Asn Ile Phe Leu Leu Gln Met Phe
    370                 375                 380

Ile Gly Val Val Asp Ile Pro Ala Lys Met Gly Ala Leu Leu Leu Leu
385                 390                 395                 400
```

-continued

```
Ser His Leu Gly Arg Arg Pro Thr Leu Ala Ala Ser Leu Leu Leu Ala
            405                 410                 415

Gly Leu Cys Ile Leu Ala Asn Thr Leu Val Pro His Glu Met Gly Ala
            420                 425                 430

Leu Arg Ser Ala Leu Ala Val Leu Gly Leu Gly Val Gly Ala Ala
            435                 440                 445

Phe Thr Cys Ile Thr Ile Tyr Ser Ser Glu Leu Phe Pro Thr Val Leu
            450                 455                 460

Arg Met Thr Ala Val Gly Leu Gly Gln Met Ala Ala Arg Gly Gly Ala
465                 470                 475                 480

Ile Leu Gly Pro Leu Val Arg Leu Leu Gly Val His Gly Pro Trp Leu
            485                 490                 495

Pro Leu Leu Val Tyr Gly Thr Val Pro Val Leu Ser Gly Leu Ala Ala
            500                 505                 510

Leu Leu Leu Pro Glu Thr Gln Ser Leu Pro Leu Pro Asp Thr Ile Gln
            515                 520                 525

Asp Val Gln Asn Gln Ala Val Lys Lys Ala Thr His Gly Thr Leu Gly
            530                 535                 540

Asn Ser Val Leu Lys Ser Thr Gln Phe
545                 550
```